United States Patent [19]

Dull et al.

[11] Patent Number: 4,937,146

[45] Date of Patent: Jun. 26, 1990

[54] RESIN-COATED ARTICLE HAVING LOW TACK

[75] Inventors: Ronald M. Dull, Coral Springs; Lawrence B. Smith, West Palm Beach, both of Fla.; Harold E. Garey, Ipswich, Mass.

[73] Assignee: Kirschner Medical Corporation, Timonium, Md.

[21] Appl. No.: 160,515

[22] Filed: Feb. 26, 1988

[51] Int. Cl.$^5$ ............................................. B32B 27/00
[52] U.S. Cl. ............................ 428/423.1; 428/423.3; 428/484; 524/488
[58] Field of Search .................. 428/423.1, 423.3, 484; 128/90; 524/488

[56] References Cited

U.S. PATENT DOCUMENTS

| | | | |
|---|---|---|---|
| 3,043,298 | 7/1962 | Brickman et al. | 128/91 |
| 3,089,486 | 5/1963 | Pike | 128/90 |
| 3,630,194 | 12/1971 | Boardman | 128/90 |
| 3,763,858 | 10/1973 | Buese | 128/156 |
| 4,454,873 | 6/1984 | Laufenberg et al. | 128/90 |
| 4,667,661 | 5/1987 | Scholz et al. | 428/425.6 |
| 4,690,842 | 9/1987 | Kammerer et al. | 428/423.3 |

*Primary Examiner*—Edith Buffalow
*Attorney, Agent, or Firm*—Frost & Jacobs

[57] ABSTRACT

A water curable resin-coated sheet useful as an orthopedic cast having a non-polar hydrophobic lubricant admixed with a resin prepolymer in the coating in order to provide low surface tack. A method of preparation involves mixing the lubricant and resin prepolymer briefly to form an unstable mixture and immediately applying the mixture to a substrate sheet of fiberglass or the like, the lubricant being present in an amount in excess of that which is miscible with the resin prepolymer.

4 Claims, No Drawings

RESIN-COATED ARTICLE HAVING LOW TACK

BACKGROUND OF THE INVENTION

The present invention relates to an article comprising a water curable resin-coated sheet having a non-polar lubricant admixed with the resin coating which provides low tack for extended periods of time and to a method for preparation thereof. Although not so limited, the article of the invention has particular utility when produced in the form of tape material for preparing an orthopedic cast or bandage.

Prior art orthopedic casting tapes are available which comprise curable resin coatings on a substrate of fiberglass, polyester, or similar synthetic or natural fabrics. The use of water-curable urethane prepolymer for orthopedic tapes of this type is well known since water is a convenient medium for use in initiating curing of the resin prepolymer.

After curing of the prepolymer is initiated by contact with water, the resins become quite tacky until cured, thus causing difficulty in molding a cast around a body member. In order to avoid this problem, the prior art has disclosed the use of various materials to reduce the tack of resin coated tape or sheet material.

U.S. Pat. No. 3,089,486, issued May 1963 to Pike discloses the use of beeswax as a tack reducing agent in forming an orthopedic structure reinforced with a methacrylate polymer.

U.S. Pat. No. 3,630,194, issued Dec. 1971 to Boardman, discloses an orthopedic bandage comprising a flexible material supporting a solid vinyl monomer which is water curable. Inorganic fillers such as calcium sulfate, calcium carbonate, bentonite, or silica are added to reduce the tack and moderate temperature rise during curing.

U.S. Pat. No. 4,454,873, issued Jun. 1984 to Laufenberg et al, discloses an orthopedic bandage material having a thermoplastic resin and polyethylene oxide applied as an anti-block agent, the polyethylene oxide being in the form of a coating on the outer surface of the material or in the resin. Talc can also be added to reduce tack.

U.S. Pat. No. 4,667,661, issued May 1987 to Scholz et al, discloses a curable resin coated sheet useful as an orthopedic bandage, comprising a water-curable resin-coated sheet having a lubricant at the surface thereof, the lubricant being hydrophilic and present in an amount sufficient to reduce the kinetic coefficient of friction of the coated surface of the sheet material to less than about 1.2. The lubricant may be selected from a wide variety of materials which may be bound to the resin or added thereto, including sulfonate groups, a polyol, a polyethoxylated fatty alcohol, an alkyl sulfate surfactant, a polymer comprised of repeating units of ethylenically unsaturated monomers such as acrylamide, vinylpyrrolidone, vinyl acetate, etc., a polysiloxane, and polyethylene oxide groups. Preferably the resin is a water curable isocyanate-functional prepolymer.

U.S. Pat. No. 4,667,661 states that hydrophobic materials were initially evaluated as lubricants, but that such materials provided only a transient reduction in tack. More specifically, corn oil, mineral oil, hydrocarbons such as hexadecane and motor oil provided a non-tacky and slippery feeling surface, but on average the slippery effect lasted only a day to a week "apparently due to dissolution of the lubricant into the resin." In contrast to this, silicone based fluids reduced the tackiness of the resin without affecting other properties of the cast and remained on the surface of the resin even at elevated temperatures (Column 8, line 47 through line 2 of column 9).

Other patents relating to the use of additives in orthopedic wrappings or casts include U.S. Pat. Nos. 3,043,298; 3,763,858 and UK Patent Application 2,092,606.

Water-curable resins suitable for use in this field include polyurethanes, cyanoacrylate esters and the like, disclosed in U.S. Pat. Nos. 4,131,114; 4,411,262; and 4,502,479.

Despite the numerous disclosures in the prior art relating to the preparation of curable resin coated sheet or tape material for use as an orthopedic bandage or cast, there is still a definite need for such a product which has long shelf life, which utilizes an inexpensive, non-toxic lubricant for the reduction of tack and which can be prepared by simple mixing of the resin prepolymer and lubricant for application to sheet material.

SUMMARY OF THE INVENTION

It is a primary object of the invention to provide a water curable resin-coated sheet having low tack, for use as an orthopedic cast or bandage, which fulfills the above need.

It is a further object of the invention to provide a method of preparing a water curable resin-coated sheet having low surface tack.

According to the invention there is provided an article comprising a water curable resin-coated sheet having a non-polar lubricant admixed with the resin coating, said lubricant being hydrophobic and incompatible with said resin to an extent such that at least part of said lubricant is at the surface of said coating whereby to provide low tack at said surface, said lubricant comprising from about 2 to about 40 parts by weight and said resin comprising from about 98 to about 60 parts by weight of the admixture.

The invention further provides a method of preparing a water-curable resin-coated sheet having low surface tack, which comprises adding a non-polar, hydrophobic lubricant to a water curable resin prepolymer in an amount in excess of that which is miscible with said prepolymer, agitating for a period of time sufficient only to form an unstable mixture of said lubricant and resin, immediately applying said mixture to the sheet, and permitting at least part of said lubricant to migrate to the surface of said mixture, whereby to provide a resin-coated sheet having low surface tack and a capability of bonding to itself when contacted with water.

The present invention further provides a method of applying an orthopedic cast to a body member comprising the steps of initiating the cure of a water curable resin-coated sheet containing from about 2 to about 40 parts by weight of a non-polar, hydrophobic lubricant in an unstable admixture with from about 98 to about 60 parts by weight of the resin in prepolymer form in the coating, wrapping said sheet around said body member after the initiation of cure, and molding the wrapped sheet about said body member whereby to obtain bonding of layers of said sheet to one another upon curing of said resin.

In the preferred practice of the invention the water curable resin is an isocyanate-functional prepolymer (e.g. urethane), and the non-polar lubricant is mineral oil, paraffin wax, microcrystalline wax, vegetable oil, animal oil, hydrogenated oils, or mixtures thereof. Preferably, from about 8 to about 20 parts by weight of the lubricant is admixed with from about 92 to about 80 parts by weight of the resin prepolymer.

DETAILED DESCRIPTION OF THE INVENTION

Contrary to the disclosure of U.S. Pat. No. 4,667,661 regarding the transient effect of materials such as corn oil, mineral oil, hydrocarbons and motor oil in providing a non-tacky surface, the present invention constitutes a discovery that such lubricants are effective and permanent, at least for a period of time up to about 1 year, if the lubricant is added in an amount in excess of that which is miscible with or soluble in the resin, and if it is mixed with the resin prepolymer immediately before coating the substrate, with the mixing being conducted for a relatively short period of time sufficient only to form an unstable admixture, resulting in separation and migration of the lubricant to the surface of the resin coated tape or sheet. Although not intending to be bound by theory, it is believed that the brief mixing and consequent instability of the admixture, as well as the incompatability of the lubricant with the resin prepolymer, diminishes subsequent dissolution or absorption of the lubricant into the resin during storage. Moreover, the relatively high proportion of lubricant in the admixture ensures that at least a portion of the lubricant remains on the surface even though some may be absorbed permanently into the resin.

The preferred resin is an isocyanate-functional prepolymer which may be prepared as described in the above-mentioned U.S. Pat. Nos. 4,131,114; 4,411,262 and 4,502,479. The disclosures of these patents are incorporated herein by reference.

More particularly, a urethane prepolymer may be prepared by reacting polyisocyanates and polyols in an equivalent ratio of from 2:1 to 12:1, and preferably from 3:1 to 5:1. Preferred aromatic polyisocyanates include tolylene diisocyanate and diphenylmethane diisocyanate. Preferred polyols include polyether and polyester polyols and dials such as polyethylene ether glycols, polytetramethylene ether glycols, polycaprolactone diols, polypropylene ether glycol and butane diol.

Suitable amine catalysts are used in amounts ranging from about 0.05% to about 10% by weight. Stabilizers of known types may be added in amounts ranging from about 0.01% to about 1% by weight, as well as conventional foam suppressors in amounts ranging from about 0.05% to about 1% by weight.

The preferred lubricants comprise mineral oil, waxes of relatively low melting point, vegetable or animal oils which are liquid at room temperature, and mixtures thereof. If a wax is used which is normally solid at room temperature, it is preferred to dissolve the wax in mineral oil so as to provide a lubricant which is liquid at room temperature. However, it is within the scope of the invention to use a solid lubricant and melt it when mixing with the resin.

Mixing of the lubricant with the resin prepolymer is effected with conventional mixing equipment of a type which does not entrain air bubbles in the admixture.

From about 2 to about 40 parts by weight of lubricant is mixed with from about 98 to about 60 parts by weight of resin polymer. Preferably, from about 8 to about 20 parts by weight of lubricant is admixed. The amount of lubricant effective in the present invention is dependent on the lipophilic characteristics of the resin prepolymer.

When using a preferred isocyanate prepolymer of the type described above, about 3% lubricant is miscible therewith. Hence, more than 3%, preferably at least about 8%, is used with such a resin.

Formulations have been prepared utilizing 10, 12.5, 17.5, 20, 22, 25 and 30 parts by weight of mineral oil. These formulations were found to have satisfactory tack and handling characteristics when curing was initiated by contact with water. A test using 50 parts by weight of mineral oil resulted in unsatisfactory handling characteristics.

Additives conventional in the art may also be incorporated in relatively minor amounts, such as talc, calcium carbonate and other materials which are inert to the resin prepolymer and lubricant, and which are non-toxic and non-irritating to the skin of a patient.

The use of polyethylene gloves when wrapping and molding the material to form a cast is preferred since the resin does not adhere thereto.

Comparative tests of tackiness have been conducted on tapes prepared in accordance with the present invention and commercially available prior art tapes. The results are set forth in the appended Table. It is significant that sample 2, which was prepared 10 months before the test, exhibited a tackiness identical to that of sample 1, which was prepared about a week before the test. Samples 1 and 2, made in accordance with the invention, exhibited far less tack than any of the commercially available products.

The tests were conducted with a polyethylene wrapped laboratory stopper connected by a wire to a scale. The surface area of the bottom of the polyethylene stopper was 0.644 square inch. The procedure involved dipping the casting tape in water, squeezing, then wrapping the sample on a 2 inch diameter mandrel. The bottom of the polyethylene covered stopper was then pressed against the curing cast and pulled away with the scale, with the highest scale reading during the cure being noted. Any resin adhereing to the polyethylene cover was removed before the next test. The results were calculated as pounds per square inch required to separate the covered stopper from the cast during cure.

When molding tapes made in accordance with the invention into orthopedic casts by dipping in water to initiate curing, it was found that the tape handled satisfactorily, exhibiting a slippery surface which did not stick to polyethylene gloves, and that the laminated layers bonded to one another upon curing.

TABLE

| Tape Sample | Tack Determination | |
|---|---|---|
| | Age of Sample | Tack Value (lb/in$^2$) |
| 1 (present invention) | 1 week | 0.05 |
| 2 (present invention) | 10 months | 0.05 |
| 3 (K-cast Improved) | 2 weeks | 0.92 |
| 4 (Delta-lite Fibreglass) | 7 months | 1.16 |
| 5 (Scotchcast Plus 3M) | 23 months | 0.34 |

Sample 1 - 10 parts by weight mineral oil, 90 parts by weight urethane prepolymer.
Sample 2 - 10 parts by weight mineral oil, 90 parts by weight urethane prepolymer.

We claim:

1. An article having improved shelf life comprising a water curable resin-coated sheet having a non-polar lubricant admixed with the resin coating, said lubricant being hydrophobic and incompatible with said resin to an extent such that at least part of said lubricant is at the surface of said coating whereby to provide low tack at said surface, said lubricant comprising from about 2 to about 40 parts by weight and said resin comprising from about 98 to about 60 parts by weight of the admixture.

2. The article claimed in claim 1, wherein said water curable resin is an isocyanate-functional prepolymer.

3. The article claimed in claim 2, wherein said lubricant comprises from about 8 to about 20 parts by weight of said admixture.

4. The article claimed in claim 1, wherein said nonpolar lubricant is selected from the group consisting of mineral oil, paraffin wax, microcrystalline wax, vegetable oil, animal oil, hydrogenated oils, and mixtures thereof.

* * * * *